US00PP24888P2

(12) United States Plant Patent
Green, Jr.

(10) Patent No.: US PP24,888 P2
(45) Date of Patent: Sep. 16, 2014

(54) ***CAMELLIA* PLANT NAMED 'GREEN 99-031'**

(50) Latin Name: *Camellia sasanqua*
Varietal Denomination: Green 99-031

(71) Applicant: Robert M. Green, Jr., Fairhope, AL (US)

(72) Inventor: Robert M. Green, Jr., Fairhope, AL (US)

(73) Assignee: Plants Nouveau, LLC, Charleston, SC (US)

( * ) Notice: Subject to any disclaimer, the term of this patent is extended or adjusted under 35 U.S.C. 154(b) by 88 days.

(21) Appl. No.: 13/815,071

(22) Filed: Jan. 29, 2013

(51) Int. Cl.
*A01H 5/00* (2006.01)

(52) U.S. Cl.
USPC ..... Plt./245

(58) Field of Classification Search
USPC ..... Plt./245
See application file for complete search history.

*Primary Examiner* — Anne Grunberg
(74) *Attorney, Agent, or Firm* — Penny J. Aguirre

(57) ABSTRACT

A new cultivar of *Camellia sasanqua* named 'Green 99-031', characterized by its dense, upright plant habit, its large deep pink double flowers (formal form) that are essentially sterile, its vigorous growth habit, its dark green foliage, and its good resistance to *Phytophora* sp. and *Glomerella*.

2 Drawing Sheets

Botanical classification: *Camellia sasanqua.*
Variety denomination: 'Green 99-031'.

CROSS REFERENCE TO A RELATED APPLICATION

This application is co-pending with a U.S. Plant Patent Application filed for a plant derived from the same breeding program that is entitled *Camellia* Plant Named 'Green 99-016' (U.S. Plant patent application Ser. No. 13/815,068).

BACKGROUND OF THE INVENTION

The present invention relates to a new and distinct cultivar of *Camellia sasanqua*. The new cultivar will be referred to hereafter by its cultivar name, 'Green 99-031'. 'Green 99-031' is grown for use as a landscape shrub.

The new *Camellia* arose from on ongoing breeding program conducted by the Inventor in Fairhope, Ala. that began in 1992. The objective of the breeding program is to produce new cultivars of *Camellia* with compact plant habits, vigorous growth habits, improved disease resistance and extended bloom periods. 'Green 99-031' originated from seed derived from open pollination of the cultivar 'Mine-No-Yuki' (not patented) in 1998. The male parent is therefore unknown. The new *Camellia* was selected as a single unique plant amongst the resulting seedlings in October of 2005.

The new cultivar was first asexually propagated by stem cutting by the Inventor in summer of 2006 in Fairhope, Ala. Asexual propagation by stem cuttings has determined that the characteristics of this cultivar are stable and are reproduced true to type in successive generations.

SUMMARY OF THE INVENTION

The following traits have been repeatedly observed and represent the characteristics of the new *Camellia* as observed in Fairhope, Ala. These attributes in combination distinguish 'Green 99-031' as a unique cultivar of *Camellia.*

1. 'Green 99-031' exhibits a dense, upright plant habit.
2. 'Green 99-031' exhibits large deep pink double flowers (formal form) that are essentially sterile.
3. 'Green 99-031' exhibits a vigorous growth habit.
4. 'Green 99-031' exhibits dark green foliage.
5. 'Green 99-031' has shown good resistance to *Phytophora* sp. and *Glomerella.*

The new cultivar of *Camellia* can be readily distinguished from its parent plant and other cultivars. 'Mine-No-Yuki', the female parent plant, differs from 'Green 99-031' in having a more open, spreading and informal plant habit and in having white flowers and lighter green foliage. 'Green 99-031' can also be compared to the cultivars 'Kanjiro' (not patented), 'Cotton Candy' (not patented) and 'Green 99-016'. 'Kanjiro' is similar to 'Green 99-031' in having a dense plant habit, good disease resistance, and in having a long blooming period. 'Kanjiro' differs from 'Green 99-031' in having flowers that are smaller, deeper pink in color and semi-double, and in having a slightly less vigorous growth habit. 'Cotton Candy' is similar to 'Green 99-031' in having dark green foliage and flowers that are similar in color (slightly darker). 'Cotton Candy' differs from 'Green 99-031' in having a less dense plant habit, less vigor, much less disease resitance and in having smaller flowers that are lighter pink in color and peony-formed. 'Green 99-016' is similar to 'Green 99-031' in having good disease restance, a dense plant habit, good vigor and dark green foliage. 'Green 99-016' differs from 'Green 99-031' in having slightly smaller flowers that are white in color, more double and peony-formed.

BRIEF DESCRIPTION OF THE DRAWING

The accompanying colored photographs illustrate the overall appearance and distinct characteristics of the new *Camellia*, 'Green 99-031', as grown in Fairhope, Ala. The photographs were taken of four year-old plants of 'Green 99-031' as grown in a trial garden in in Fairhope, Ala.

Figure 1:
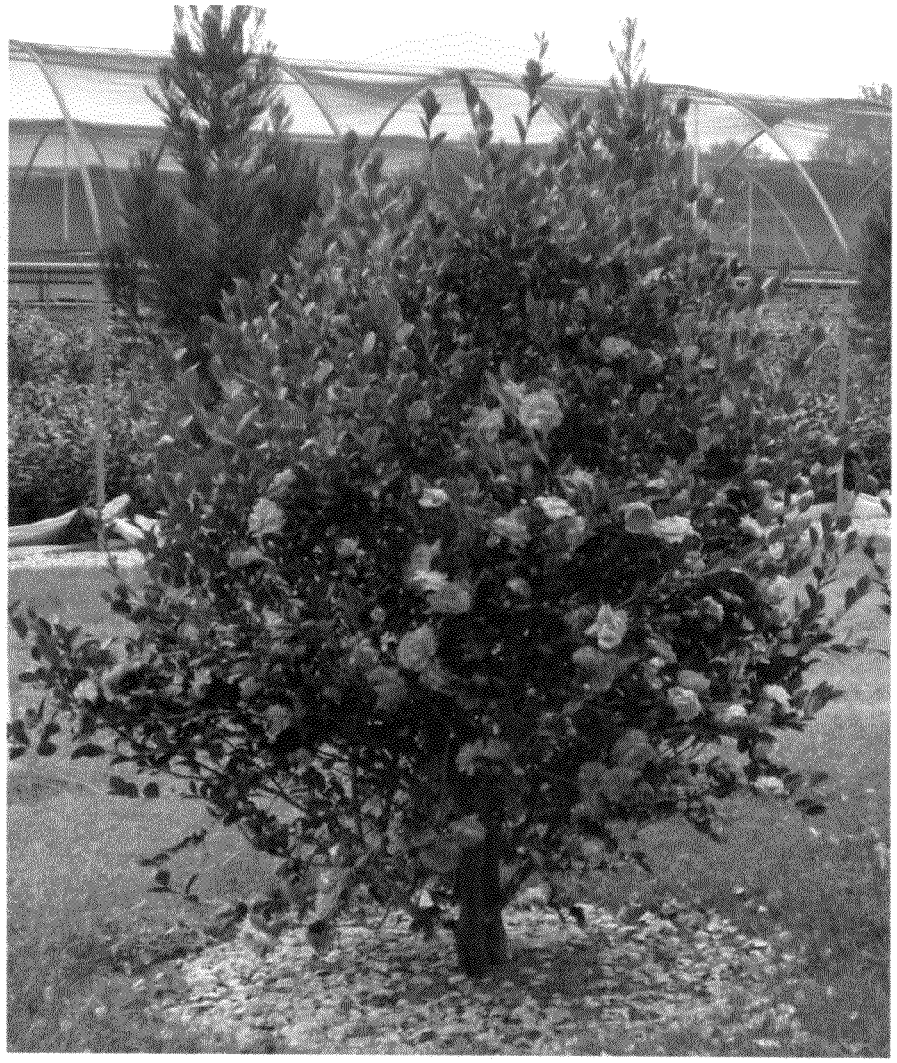
FIG. 1 provides view of the plant habit of 'Green 99-031'.
Figure 2:
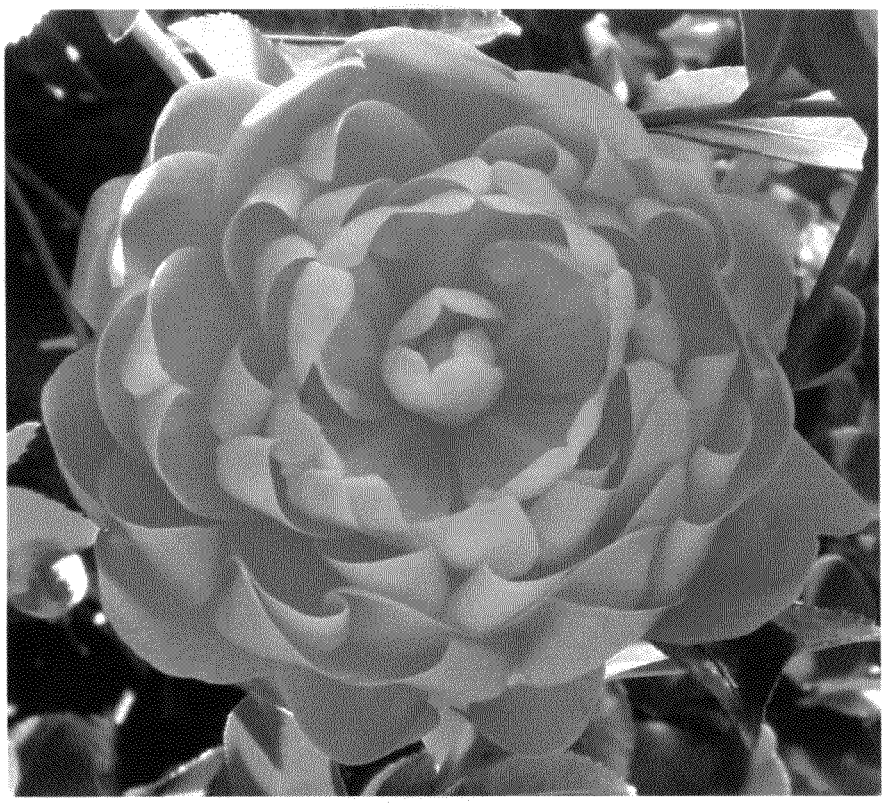
FIG. 2 provides a close-up view of a flower of 'Green 99-031'.

The colors in the photographs are as close as possible with digital photography techniques available, the color values cited in the detailed botanical description accurately describe the colors of the new *Camellia*.

DETAILED BOTANICAL DESCRIPTION

The following is a detailed description of the new cultivar as observed on 42 month-old plants of 'Green 99-031' as grown outdoors under 30% shade cloth in 3-gallon containers in Fairhope, Ala. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming habit.*—Seven to eight weeks in mid to late fall in Fairhope, Ala.

*Plant type.*—Evergreen shrub.

*Plant habit.*—Dense and upright.

*Height and spread.*—About 3.1 m (10 feet) in height and up to 1.8 m (6 feet) in width.

*Cold hardiness.*—At least in U.S.D.A. Zones 7a to 9.

*Diseases and pests.*—Has shown resistance to *Phytophora* sp. and *Glomerella*.

*Propagation.*—Stem cuttings.

*Growth rate.*—Very vigorous.

Branch description:

*Stem shape.*—Round.

*Stem strength.*—Strong.

*Stem color.*—Young; 165A, mature bark; 200A flushed with 165A at the base then becoming 166B towards the middle of the branches.

*Stem size.*—Lateral branches; 41 to 46 cm in length and 3 mm in width.

*Stem surface.*—Young; bark-like, slightly glossy and sparsely covered with soft pubescent hairs 0.5 mm in length and 165A in color, mature; bark-like, slightly rough to touch.

*Branching.*—Densely branched with an average of 18 lateral branches.

Foliage description:

*Leaf shape.*—Varies between elliptic (sometimes oval).

*Leaf division.*—Simple.

*Leaf base.*—Cuneate.

*Leaf apex.*—Varies between bluntly acuminate and acute.

*Leaf fragrance.*—None.

*Leaf margins.*—Serrate.

*Leaf arrangement.*—Alternate.

*Leaf attachment.*—Petiolate.

*Leaf substance.*—Young leaves are think and rubbery, mature leaves are thick.

*Leaf surface.*—Smooth and glabrous on both surfaces, very glossy on upper surface, satiny on lower surface.

*Leaf size.*—Average of 2 cm in length and 1.5 cm in width.

*Leaf quantity.*—Average of 15 per branch 40 cm in length.

*Leaf venation.*—Pinnate, upper surface mid rib 146C in color, lower surface mid rib 145A, other veins match leaf coloration.

*Leaf color.*—Young and mature leaves upper surface; a blend of 139A and N137A, young and mature leaves lower surface; 146A.

*Petioles.*—Flattened with a width of 1 mm and a length of 3 mm, glabrous surface, 144A in color.

*Stipules.*—None.

Inflorescence description:

*Inflorescence type.*—Solitary.

*Flower number.*—6 to 8 per lateral stem.

*Flower fragrance.*—Slightly fragrant.

*Flower longevity.*—About one week, self cleaning.

*Flower type.*—Formal double.

*Flower aspect.*—Outward to slightly upright.

*Flower size.*—Average of 9.5 cm in diameter and 3 cm in depth.

*Peduncles.*—None, flowers are sessile to stem.

*Flower buds.*—Globose in shape, average of 2 cm in length and width, color 144B, apex 70A.

*Sepals.*—Average of 6, ovate-rounded in shape and strongly cupped inward, imbricate, margin is entire, color of upper and lower surface; 144B, base 145C, margins 70A, both surfaces are glabrous and satiny, average of 1.2 cm in length and 1 cm in width, apex is obtuse, base is truncate.

*Petals.*—35 to 39, cordate-oblong to cordate in shape, upper and lower surface is glabrous and dull, margin entire, apex cordate, broadly cuneate base, average of 2.5 cm in length and and 2.4 cm width, color: opening flowers upper and lower surface; a blend of 70A and 70B, color of fully open flowers upper and lower surface; a blend of 70B, 70C and 70D.

Reproductive organs:

*Pistil.*—None observed.

*Stamens.*—Just a few sparse mal-formed stamens about 4 mm in length and 155A in color, essentially sterile.

*Fruit and seed.*—Very few fruit if any are formed, none available for data collection.

It is claimed:

1. A new and distinct cultivar of *Camellia* plant named 'Green 99-031' as herein illustrated and described.

* * * * *